(12) United States Patent
Diedering et al.

(10) Patent No.: US 11,857,441 B2
(45) Date of Patent: Jan. 2, 2024

(54) STENT LOADING DEVICE

(71) Applicant: 4C Medical Technologies, Inc., Brooklyn Park, MN (US)

(72) Inventors: Jason S. Diedering, Minneapolis, MN (US); Saravana B. Kumar, Minnetonka, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 0 days.

(21) Appl. No.: 16/559,055

(22) Filed: Sep. 3, 2019

(65) Prior Publication Data
US 2020/0069449 A1 Mar. 5, 2020

Related U.S. Application Data

(60) Provisional application No. 62/726,602, filed on Sep. 4, 2018.

(51) Int. Cl.
*A61F 2/95* (2013.01)
*A61F 2/24* (2006.01)
*A61F 2/958* (2013.01)

(52) U.S. Cl.
CPC .............. *A61F 2/95* (2013.01); *A61F 2/2466* (2013.01); *A61F 2/9525* (2020.05); *A61F 2/958* (2013.01);
(Continued)

(58) Field of Classification Search
CPC ........ A61F 2/95; A61F 2/9525; A61F 2/2466; A61F 2/9522; A61F 2230/0017;
(Continued)

(56) References Cited

U.S. PATENT DOCUMENTS

| 4,424,833 A | 1/1984 | Spector |
| 4,503,569 A | 3/1985 | Dotter |

(Continued)

FOREIGN PATENT DOCUMENTS

| AU | 2014203064 B2 | 6/2015 |
| AU | 2015230879 A1 | 10/2015 |

(Continued)

OTHER PUBLICATIONS

International Search Report and Written Opinion issued in related PCT application No. PCT/US2019/049410, dated Dec. 13, 2019.
(Continued)

*Primary Examiner* — Timothy J Neal
*Assistant Examiner* — Andrew P. Restaino
(74) *Attorney, Agent, or Firm* — Weiss & Arons LLP

(57) ABSTRACT

A device and method for predictably and controlling the collapsing of a collapsible and expandable stent for subsequent translation through a delivery sheath lumen to an anatomical target such as a heart valve or intravascular location for expansion and implantation. The loading device defines in inner lumen comprising a successively decreasing, from the proximal to the distal direction, inner diameter to a region of constant inner diameter wherein the stent is in a collapsed configuration. The device and method may provide for an at least partially collapsed configuration of the stent that may be further collapsed as a part of the implantation procedure and may comprise a stent that is pre-loaded for future use.

6 Claims, 5 Drawing Sheets

(52) U.S. Cl.
CPC ..... *A61F 2/9522* (2020.05); *A61F 2210/0014* (2013.01); *A61F 2230/0017* (2013.01); *A61F 2230/0071* (2013.01)

(58) Field of Classification Search
CPC .............. A61F 2210/0014; A61F 2/958; A61F 2230/0071; A61F 2/2436; A61F 2/2418
See application file for complete search history.

(56) References Cited

U.S. PATENT DOCUMENTS

| | | | |
|---|---|---|---|
| 4,733,665 A | 3/1988 | Palmaz | |
| 4,878,906 A | 11/1989 | Lindemann | |
| 5,190,528 A | 3/1993 | Fonger | |
| 5,415,667 A | 5/1995 | Frater | |
| 5,441,483 A | 8/1995 | Avitall | |
| 5,693,083 A | 12/1997 | Baker | |
| 5,693,089 A | 12/1997 | Inoue | |
| 5,776,188 A | 7/1998 | Shepherd | |
| 5,843,090 A | 12/1998 | Schuetz | |
| 5,928,258 A * | 7/1999 | Khan | A61F 2/9525 606/191 |
| 5,957,949 A | 9/1999 | Leonhardt | |
| 5,968,070 A | 10/1999 | Bley | |
| 6,123,723 A | 9/2000 | Konya | |
| 6,152,144 A | 11/2000 | Lesh | |
| 6,231,602 B1 | 5/2001 | Carpentier | |
| 6,287,334 B1 | 9/2001 | Moll | |
| 6,319,280 B1 | 11/2001 | Schoon | |
| 6,319,281 B1 | 11/2001 | Patel | |
| 6,332,893 B1 | 12/2001 | Mortier | |
| 6,371,983 B1 | 4/2002 | Lane | |
| 6,409,758 B2 | 6/2002 | Stobie | |
| 6,425,916 B1 | 7/2002 | Garrison | |
| 6,471,718 B1 | 10/2002 | Staehle et al. | |
| 6,494,909 B2 | 12/2002 | Greenhalgh | |
| 6,503,272 B2 | 1/2003 | Duerig | |
| 6,540,782 B1 | 4/2003 | Snyders | |
| 6,569,196 B1 | 5/2003 | Vesely | |
| 6,589,275 B1 | 7/2003 | Ivancev | |
| 6,702,826 B2 | 3/2004 | Liddicoat | |
| 6,738,655 B1 | 5/2004 | Sen | |
| 6,790,231 B2 | 9/2004 | Liddicoat | |
| 6,790,237 B2 | 9/2004 | Stinson | |
| 6,821,297 B2 | 11/2004 | Snyders | |
| 6,830,585 B1 | 12/2004 | Artof | |
| 6,840,957 B2 | 1/2005 | DiMatteo | |
| 6,875,231 B2 | 4/2005 | Anduiza | |
| 7,011,671 B2 | 3/2006 | Welch | |
| 7,041,132 B2 | 5/2006 | Quijano | |
| 7,044,966 B2 | 5/2006 | Svanidze | |
| 7,125,420 B2 | 10/2006 | Rourke | |
| 7,153,324 B2 | 12/2006 | Case | |
| 7,252,682 B2 | 8/2007 | Seguin | |
| 7,276,077 B2 | 10/2007 | Zadno-Azizi | |
| 7,276,078 B2 | 10/2007 | Spenser | |
| 7,291,168 B2 | 11/2007 | Macoviak | |
| 7,364,588 B2 | 4/2008 | Mathis | |
| 7,381,220 B2 | 6/2008 | Macoviak | |
| 7,442,204 B2 | 10/2008 | Schwammenthal | |
| 7,445,631 B2 | 11/2008 | Salahieh | |
| 7,455,689 B2 | 11/2008 | Johnson | |
| 7,510,572 B2 | 3/2009 | Gabbay | |
| 7,524,331 B2 | 4/2009 | Birdsall | |
| 7,611,534 B2 | 11/2009 | Kapadia | |
| 7,704,277 B2 | 4/2010 | Zakay | |
| 7,749,266 B2 | 7/2010 | Forster | |
| 7,758,491 B2 | 7/2010 | Buckner | |
| 7,780,723 B2 | 8/2010 | Taylor | |
| 7,789,909 B2 | 9/2010 | Andersen | |
| 7,935,144 B2 | 5/2011 | Robin | |
| 7,959,672 B2 | 6/2011 | Salahieh | |
| 7,967,853 B2 | 6/2011 | Eidenschink | |
| 7,998,196 B2 | 8/2011 | Mathison | |
| 8,012,201 B2 | 9/2011 | Lashinski | |
| 8,016,877 B2 | 9/2011 | Seguin | |
| 8,021,420 B2 | 9/2011 | Dolan | |
| 8,029,556 B2 | 10/2011 | Rowe | |
| D648,854 S | 11/2011 | Braido | |
| 8,052,592 B2 | 11/2011 | Goldfarb | |
| 8,057,493 B2 | 11/2011 | Goldfarb | |
| 8,070,802 B2 | 12/2011 | Lamphere | |
| 8,083,793 B2 | 12/2011 | Lane | |
| D653,341 S | 1/2012 | Braido | |
| D653,342 S | 1/2012 | Braido | |
| 8,092,524 B2 | 1/2012 | Nugent | |
| 8,142,492 B2 | 3/2012 | Forster | |
| 8,147,541 B2 | 4/2012 | Forster | |
| D660,433 S | 5/2012 | Braido | |
| D660,967 S | 5/2012 | Braido | |
| 8,167,932 B2 | 5/2012 | Bourang | |
| 8,236,049 B2 | 8/2012 | Rowe | |
| 8,246,677 B2 | 8/2012 | Ryan | |
| 8,252,051 B2 | 8/2012 | Chau | |
| 8,287,538 B2 | 10/2012 | Brenzel et al. | |
| 8,308,798 B2 | 11/2012 | Pintor | |
| 8,348,998 B2 | 1/2013 | Pintor | |
| 8,348,999 B2 | 1/2013 | Kheradvar | |
| 8,366,768 B2 | 2/2013 | Zhang | |
| 8,398,708 B2 | 3/2013 | Meiri | |
| 8,409,275 B2 | 4/2013 | Matheny | |
| 8,414,645 B2 | 4/2013 | Dwork | |
| 8,439,970 B2 | 5/2013 | Jimenez | |
| 8,454,686 B2 | 6/2013 | Alkhatib | |
| 8,465,541 B2 | 6/2013 | Dwork | |
| 8,491,650 B2 | 7/2013 | Wiemeyer | |
| 8,512,400 B2 | 8/2013 | Tran | |
| 8,518,106 B2 | 8/2013 | Duffy | |
| 8,535,373 B2 | 9/2013 | Stacchino | |
| 8,562,673 B2 | 10/2013 | Yeung | |
| 8,568,472 B2 | 10/2013 | Marchand | |
| 8,579,963 B2 | 11/2013 | Tabor | |
| 8,579,964 B2 | 11/2013 | Lane | |
| 8,603,159 B2 | 12/2013 | Seguin | |
| 8,623,075 B2 | 1/2014 | Murray, III et al. | |
| 8,636,764 B2 | 1/2014 | Miles | |
| 8,641,757 B2 | 2/2014 | Pintor | |
| 8,657,870 B2 | 2/2014 | Turovskiy | |
| 8,663,318 B2 | 3/2014 | Ho | |
| 8,679,176 B2 | 3/2014 | Matheny | |
| 8,721,715 B2 | 5/2014 | Wang | |
| 8,740,976 B2 | 6/2014 | Tran | |
| 8,747,459 B2 | 6/2014 | Nguyen | |
| 8,747,461 B2 | 6/2014 | Centola | |
| 8,764,793 B2 | 7/2014 | Lee | |
| 8,764,820 B2 | 7/2014 | Dehdashtian | |
| 8,778,020 B2 | 7/2014 | Gregg | |
| 8,790,396 B2 | 7/2014 | Bergheim | |
| 8,795,354 B2 | 8/2014 | Benichou | |
| 8,795,357 B2 | 8/2014 | Yohanan | |
| 8,805,466 B2 | 8/2014 | Salahieh | |
| 8,814,931 B2 | 8/2014 | Wang | |
| 8,828,043 B2 | 9/2014 | Chambers | |
| 8,828,051 B2 | 9/2014 | Javois | |
| 8,845,711 B2 | 9/2014 | Miles | |
| 8,845,722 B2 | 9/2014 | Gabbay | |
| 8,852,271 B2 | 10/2014 | Murray, III et al. | |
| 8,852,272 B2 | 10/2014 | Gross | |
| 8,870,949 B2 | 10/2014 | Rowe | |
| 8,876,897 B2 | 11/2014 | Kheradvar | |
| 8,906,022 B2 | 12/2014 | Krinke et al. | |
| 8,926,692 B2 | 1/2015 | Dwork | |
| 8,956,402 B2 | 2/2015 | Cohn | |
| 8,956,405 B2 | 2/2015 | Wang | |
| 8,961,518 B2 | 2/2015 | Kyle et al. | |
| 8,986,372 B2 | 3/2015 | Murry, III | |
| 8,986,374 B2 | 3/2015 | Cao | |
| 8,986,375 B2 | 3/2015 | Garde | |
| 8,998,980 B2 | 4/2015 | Shipley | |
| 8,998,982 B2 | 4/2015 | Richter | |
| 9,005,273 B2 | 4/2015 | Salahieh | |
| 9,011,527 B2 | 4/2015 | Li | |
| D730,520 S | 5/2015 | Braido | |
| D730,521 S | 5/2015 | Braido | |

(56) References Cited

U.S. PATENT DOCUMENTS

| | | |
|---|---|---|
| 9,023,101 B2 | 5/2015 | Krahbichler |
| 9,050,188 B2 | 6/2015 | Schweich, Jr. |
| 9,060,855 B2 | 6/2015 | Tuval |
| 9,060,857 B2 | 6/2015 | Nguyen |
| 9,060,858 B2 | 6/2015 | Thornton |
| 9,061,119 B2 | 6/2015 | Le |
| 9,066,800 B2 | 6/2015 | Clague |
| 9,072,603 B2 | 7/2015 | Tuval |
| 9,101,471 B2 | 8/2015 | Kleinschrodt |
| 9,119,717 B2 | 9/2015 | Wang |
| 9,132,008 B2 | 9/2015 | Dwork |
| 9,132,009 B2 | 9/2015 | Hacohen |
| 9,138,313 B2 | 9/2015 | McGuckin, Jr. |
| 9,144,493 B2 | 9/2015 | Carr |
| 9,144,494 B2 | 9/2015 | Murray |
| 9,155,619 B2 | 10/2015 | Liu |
| 9,161,835 B2 | 10/2015 | Rankin |
| 9,173,737 B2 | 11/2015 | Hill |
| 9,192,466 B2 | 11/2015 | Kovalsky |
| 9,226,820 B2 | 1/2016 | Braido |
| 9,232,942 B2 | 1/2016 | Seguin |
| 9,232,996 B2 | 1/2016 | Sun |
| 9,248,016 B2 | 2/2016 | Oba |
| 9,259,315 B2 | 2/2016 | Zhou |
| 9,271,856 B2 | 3/2016 | Duffy |
| 9,277,993 B2 | 3/2016 | Gamarra |
| 9,289,289 B2 | 3/2016 | Rolando |
| 9,289,292 B2 | 3/2016 | Anderl |
| 9,295,547 B2 | 3/2016 | Costello |
| 9,295,549 B2 | 3/2016 | Braido |
| 9,301,836 B2 | 4/2016 | Buchbinder |
| 9,301,839 B2 | 4/2016 | Stante |
| 9,320,597 B2 | 4/2016 | Savage |
| 9,320,599 B2 | 4/2016 | Salahieh |
| 9,326,853 B2 | 5/2016 | Olson |
| 9,326,854 B2 | 5/2016 | Casley |
| 9,333,075 B2 | 5/2016 | Biadillah |
| 9,345,572 B2 | 5/2016 | Cerf |
| 9,351,831 B2 | 5/2016 | Braido |
| 9,358,108 B2 | 6/2016 | Bortlein |
| 9,364,325 B2 | 6/2016 | Alon |
| 9,364,637 B2 | 6/2016 | Rothstein |
| 9,370,422 B2 | 6/2016 | Wang |
| 9,387,106 B2 | 7/2016 | Stante |
| 9,402,720 B2 | 8/2016 | Richter |
| 9,414,910 B2 | 8/2016 | Lim |
| 9,414,917 B2 | 8/2016 | Young |
| 9,427,316 B2 | 8/2016 | Schweich, Jr. |
| 9,439,763 B2 | 9/2016 | Geist |
| 9,439,795 B2 | 9/2016 | Wang |
| 9,480,560 B2 | 11/2016 | Quadri |
| 9,498,370 B2 | 11/2016 | Kyle et al. |
| 9,504,569 B2 | 11/2016 | Malewicz |
| 9,522,062 B2 | 12/2016 | Tuval |
| 9,566,152 B2 | 2/2017 | Schweich, Jr. |
| 9,579,194 B2 | 2/2017 | Elizondo |
| 9,579,197 B2 | 2/2017 | Duffy |
| 9,622,863 B2 | 4/2017 | Karapetian |
| 9,717,592 B2 | 8/2017 | Thapliyal |
| 9,730,791 B2 | 8/2017 | Ratz |
| 9,737,400 B2 | 8/2017 | Fish |
| 9,737,401 B2 | 8/2017 | Conklin |
| 9,750,604 B2 | 9/2017 | Naor |
| 9,763,780 B2 | 9/2017 | Morriss |
| 9,795,477 B2 | 10/2017 | Tran |
| 9,801,711 B2 | 10/2017 | Gainor |
| 9,827,093 B2 | 11/2017 | Cartledge |
| 9,839,517 B2 | 12/2017 | Centola |
| 9,839,765 B2 | 12/2017 | Morris |
| 9,861,477 B2 | 1/2018 | Backus |
| 9,872,765 B2 | 1/2018 | Zeng |
| 9,877,830 B2 | 1/2018 | Lim |
| 9,968,443 B2 | 5/2018 | Bruchman |
| 10,004,601 B2 | 6/2018 | Tuval |
| 10,016,274 B2 | 7/2018 | Tabor |
| 10,016,275 B2 * | 7/2018 | Nyuli ............... A61F 2/2418 |
| 10,022,132 B2 | 7/2018 | Wlodarski et al. |
| 10,034,750 B2 | 7/2018 | Morriss |
| 10,039,637 B2 | 8/2018 | Maimon |
| 10,039,642 B2 | 8/2018 | Hillukka |
| 10,098,735 B2 | 10/2018 | Lei |
| 10,098,763 B2 | 10/2018 | Lei |
| 10,117,742 B2 | 11/2018 | Braido |
| 10,143,551 B2 | 12/2018 | Braido |
| 10,182,907 B2 | 1/2019 | Lapeyre |
| 10,195,023 B2 | 2/2019 | Wrobel |
| 10,226,340 B2 | 3/2019 | Keren |
| 10,231,834 B2 | 3/2019 | Keidar |
| 10,238,490 B2 | 3/2019 | Gifford, III |
| 10,245,145 B2 | 4/2019 | Mantanus |
| 10,258,464 B2 | 4/2019 | Delaloye |
| 10,299,917 B2 | 5/2019 | Morriss |
| 10,321,990 B2 | 6/2019 | Braido |
| 10,327,892 B2 | 6/2019 | O'Connor |
| 10,327,893 B2 | 6/2019 | Maiorano |
| 10,350,065 B2 | 7/2019 | Quadri |
| 10,357,360 B2 | 7/2019 | Hariton |
| 10,368,982 B2 | 8/2019 | Weber |
| 10,376,363 B2 | 8/2019 | Quadri |
| 10,383,725 B2 | 8/2019 | Chambers |
| 10,390,943 B2 | 8/2019 | Hernandez |
| 10,405,974 B2 | 9/2019 | Hayes |
| 10,433,961 B2 | 10/2019 | McLean |
| 10,470,880 B2 | 11/2019 | Braido |
| 10,492,907 B2 | 12/2019 | Duffy |
| 10,500,041 B2 | 12/2019 | Valdez |
| 10,507,107 B2 | 12/2019 | Nathe |
| 10,512,537 B2 | 12/2019 | Corbett |
| 10,512,538 B2 | 12/2019 | Alkhatib |
| 10,517,726 B2 | 12/2019 | Chau |
| 10,524,902 B2 | 1/2020 | Gründeman |
| 10,524,910 B2 | 1/2020 | Hammer |
| 10,531,951 B2 | 1/2020 | Spargias |
| 10,537,427 B2 | 1/2020 | Zeng |
| 10,555,809 B2 | 2/2020 | Hastings |
| 10,555,812 B2 | 2/2020 | Duffy |
| 10,561,495 B2 | 2/2020 | Chambers |
| 10,595,992 B2 | 3/2020 | Chambers |
| 10,610,362 B2 | 4/2020 | Quadri |
| 10,653,523 B2 | 5/2020 | Chambers |
| 10,667,905 B2 | 6/2020 | Ekvall |
| 10,667,909 B2 | 6/2020 | Richter |
| 10,702,379 B2 | 7/2020 | Garde |
| 10,702,380 B2 | 7/2020 | Morriss |
| 10,709,560 B2 | 7/2020 | Kofidis |
| 10,751,169 B2 | 8/2020 | Chambers |
| 10,751,170 B2 | 8/2020 | Richter |
| 10,751,172 B2 | 8/2020 | Para |
| 10,758,265 B2 | 9/2020 | Siegel |
| 10,758,342 B2 | 9/2020 | Chau |
| 10,779,935 B2 | 9/2020 | Scorsin |
| 10,779,936 B2 | 9/2020 | Pollak |
| 10,779,968 B2 | 9/2020 | Giasolli |
| 10,786,351 B2 | 9/2020 | Christianson |
| 10,828,152 B2 | 11/2020 | Chambers |
| 10,856,983 B2 | 12/2020 | Keränen |
| 10,869,756 B2 | 12/2020 | Al-Jilaihawi |
| 10,874,513 B2 | 12/2020 | Chambers |
| 10,945,835 B2 | 3/2021 | Morriss |
| 10,973,630 B2 | 4/2021 | Torrianni |
| 10,980,636 B2 | 4/2021 | Delaloye |
| 11,000,000 B2 | 5/2021 | Diedering |
| 11,007,053 B2 | 5/2021 | Braido |
| 11,007,054 B2 | 5/2021 | Braido |
| 11,013,599 B2 | 5/2021 | Subramanian |
| 11,026,782 B2 | 6/2021 | Chambers |
| 11,033,275 B2 | 6/2021 | Franano et al. |
| 11,045,202 B2 | 6/2021 | Amplatz |
| 11,065,113 B2 | 7/2021 | Backus |
| 11,065,116 B2 | 7/2021 | Tegels |
| 11,065,138 B2 | 7/2021 | Schreck |
| 11,096,781 B2 | 8/2021 | Gurovich |
| 11,147,666 B2 | 10/2021 | Braido |
| 11,154,239 B2 | 10/2021 | Toth |

(56) References Cited

U.S. PATENT DOCUMENTS

| | | |
|---|---|---|
| 11,154,396 B2 | 10/2021 | Dibie |
| 11,154,398 B2 | 10/2021 | Straubinger |
| 11,197,754 B2 | 12/2021 | Saffari |
| 11,207,176 B2 | 12/2021 | Delaloye |
| 11,278,399 B2 | 3/2022 | Liu |
| 11,278,406 B2 | 3/2022 | Straubinger |
| 11,351,028 B2 | 6/2022 | Peterson |
| 11,389,293 B2 | 7/2022 | Torrianni |
| 11,395,734 B2 | 7/2022 | Lee |
| 11,413,141 B2 | 8/2022 | Morin |
| 11,419,716 B2 | 8/2022 | Braido |
| 11,452,628 B2 | 9/2022 | Diedering |
| 11,458,013 B2 | 10/2022 | Righini |
| 2001/0005787 A1 | 6/2001 | Oz |
| 2002/0072710 A1 | 6/2002 | Stewart |
| 2002/0161377 A1 | 10/2002 | Rabkin |
| 2003/0057156 A1 | 3/2003 | Peterson |
| 2003/0083730 A1* | 5/2003 | Stinson ............... A61F 2/95 623/1.11 |
| 2003/0199971 A1 | 10/2003 | Tower |
| 2003/0225445 A1* | 12/2003 | Derus ............... A61F 2/95 623/1.11 |
| 2003/0233141 A1 | 12/2003 | Israel |
| 2004/0073286 A1 | 4/2004 | Armstrong et al. |
| 2004/0088041 A1 | 5/2004 | Stanford |
| 2004/0210307 A1 | 10/2004 | Khairkhahan |
| 2004/0243107 A1 | 12/2004 | Macoviak |
| 2005/0004641 A1 | 1/2005 | Pappu |
| 2005/0075727 A1 | 4/2005 | Wheatley |
| 2005/0096739 A1 | 5/2005 | Cao |
| 2005/0113861 A1 | 5/2005 | Corcoran |
| 2005/0197694 A1 | 9/2005 | Pai |
| 2005/0273160 A1 | 12/2005 | Lashinski |
| 2006/0142847 A1 | 6/2006 | Shaknovich |
| 2006/0184226 A1 | 8/2006 | Austin |
| 2006/0224183 A1 | 10/2006 | Freudenthal |
| 2006/0229708 A1 | 10/2006 | Powell |
| 2006/0271173 A1 | 11/2006 | Delgado, III |
| 2006/0276874 A1 | 12/2006 | Wilson |
| 2007/0016288 A1 | 1/2007 | Gurskis |
| 2007/0173930 A1 | 7/2007 | Sogard |
| 2007/0233223 A1 | 10/2007 | Styrc |
| 2007/0238979 A1 | 10/2007 | Huynh |
| 2007/0239254 A1 | 10/2007 | Chia |
| 2007/0239271 A1 | 10/2007 | Nguyen |
| 2007/0270931 A1 | 11/2007 | Leanna et al. |
| 2007/0275027 A1 | 11/2007 | Wen et al. |
| 2007/0293942 A1 | 12/2007 | Mirzaee |
| 2008/0039928 A1 | 2/2008 | Peacock |
| 2008/0082166 A1 | 4/2008 | Styrc |
| 2008/0262592 A1 | 10/2008 | Jordan |
| 2008/0269877 A1 | 10/2008 | Jenson |
| 2008/0275540 A1 | 11/2008 | Wen |
| 2008/0281398 A1 | 11/2008 | Koss |
| 2008/0288042 A1* | 11/2008 | Purdy ............... A61F 2/95 623/1.11 |
| 2008/0288055 A1 | 11/2008 | Paul, Jr. |
| 2009/0076585 A1 | 3/2009 | Hendriksen |
| 2009/0082840 A1 | 3/2009 | Rusk |
| 2009/0099640 A1 | 4/2009 | Weng |
| 2009/0099647 A1 | 4/2009 | Glimsdale |
| 2009/0125096 A1 | 5/2009 | Chu |
| 2009/0143852 A1 | 6/2009 | Chambers |
| 2009/0171447 A1 | 7/2009 | Von Segesser |
| 2009/0171456 A1 | 7/2009 | Kveen |
| 2009/0198315 A1 | 8/2009 | Boudjemline |
| 2009/0248134 A1 | 10/2009 | Dierking |
| 2009/0248143 A1 | 10/2009 | Laham |
| 2009/0270967 A1 | 10/2009 | Fleming III |
| 2009/0276039 A1 | 11/2009 | Meretei |
| 2009/0281609 A1 | 11/2009 | Benichou |
| 2010/0021726 A1 | 1/2010 | Jo |
| 2010/0057192 A1 | 3/2010 | Celermajer |
| 2010/0069948 A1 | 3/2010 | Veznedaroglu |
| 2010/0168839 A1 | 7/2010 | Braido |
| 2010/0174355 A1 | 7/2010 | Boyle |
| 2010/0217260 A1 | 8/2010 | Aramayo |
| 2010/0217261 A1 | 8/2010 | Watson |
| 2010/0217262 A1 | 8/2010 | Stevenson |
| 2010/0217263 A1 | 8/2010 | Tukulj-Popovic |
| 2010/0217264 A1 | 8/2010 | Odom |
| 2010/0217265 A1 | 8/2010 | Chen |
| 2010/0217266 A1 | 8/2010 | Helevirta |
| 2010/0217267 A1 | 8/2010 | Bergin |
| 2010/0217268 A1 | 8/2010 | Bloebaum |
| 2010/0217269 A1 | 8/2010 | Landes |
| 2010/0256749 A1 | 10/2010 | Tran |
| 2010/0262157 A1 | 10/2010 | Silver et al. |
| 2011/0022151 A1 | 1/2011 | Shin |
| 2011/0046712 A1 | 2/2011 | Melsheimer |
| 2011/0082539 A1 | 4/2011 | Suri |
| 2011/0082540 A1 | 4/2011 | Forster |
| 2011/0208293 A1 | 8/2011 | Tabor |
| 2011/0218585 A1 | 9/2011 | Krinke et al. |
| 2011/0251676 A1 | 10/2011 | Sweeney |
| 2011/0269051 A1 | 11/2011 | Wijenberg |
| 2011/0301702 A1 | 12/2011 | Rust |
| 2011/0319988 A1 | 12/2011 | Schankereli |
| 2011/0319991 A1 | 12/2011 | Hariton |
| 2012/0016468 A1 | 1/2012 | Robin |
| 2012/0035719 A1 | 2/2012 | Forster |
| 2012/0078356 A1 | 3/2012 | Fish |
| 2012/0083875 A1 | 4/2012 | Johnson et al. |
| 2012/0095551 A1 | 4/2012 | Navia |
| 2012/0101567 A1 | 4/2012 | Jansen |
| 2012/0101571 A1 | 4/2012 | Thambar |
| 2012/0109079 A1 | 5/2012 | Asleson |
| 2012/0197390 A1 | 8/2012 | Alkhatib |
| 2012/0209375 A1 | 8/2012 | Madrid |
| 2012/0226130 A1 | 9/2012 | De Graff |
| 2012/0303048 A1 | 11/2012 | Manasse |
| 2012/0323313 A1 | 12/2012 | Seguin |
| 2013/0023852 A1 | 1/2013 | Drasler |
| 2013/0060329 A1 | 3/2013 | Agnew |
| 2013/0066419 A1 | 3/2013 | Gregg |
| 2013/0079872 A1 | 3/2013 | Gallagher |
| 2013/0090728 A1 | 4/2013 | Solem |
| 2013/0096671 A1 | 4/2013 | Iobbi |
| 2013/0123911 A1 | 5/2013 | Chalekian |
| 2013/0138138 A1 | 5/2013 | Clark |
| 2013/0150956 A1 | 6/2013 | Yohanan |
| 2013/0184811 A1 | 7/2013 | Rowe |
| 2013/0190861 A1 | 7/2013 | Chau |
| 2013/0204311 A1 | 8/2013 | Kunis |
| 2013/0204360 A1 | 8/2013 | Gainor |
| 2013/0226286 A1 | 8/2013 | Hargreaves |
| 2013/0231736 A1 | 9/2013 | Essinger |
| 2013/0238089 A1 | 9/2013 | Lichtenstein |
| 2013/0297010 A1 | 11/2013 | Bishop |
| 2013/0297012 A1 | 11/2013 | Willard |
| 2013/0304197 A1 | 11/2013 | Buchbinder |
| 2013/0310917 A1 | 11/2013 | Richter |
| 2013/0310923 A1 | 11/2013 | Kheradvar |
| 2013/0317598 A1 | 11/2013 | Rowe |
| 2013/0331933 A1 | 12/2013 | Alkhatib |
| 2014/0005768 A1 | 1/2014 | Thomas |
| 2014/0005773 A1 | 1/2014 | Wheatley |
| 2014/0005778 A1 | 1/2014 | Buchbinder |
| 2014/0012371 A1 | 1/2014 | Li |
| 2014/0018841 A1 | 1/2014 | Peiffer |
| 2014/0018906 A1 | 1/2014 | Rafiee |
| 2014/0031928 A1 | 1/2014 | Murphy |
| 2014/0031951 A1 | 1/2014 | Costello |
| 2014/0039613 A1 | 2/2014 | Navia |
| 2014/0046433 A1 | 2/2014 | Kovalsky |
| 2014/0046436 A1 | 2/2014 | Kheradvar |
| 2014/0052238 A1 | 2/2014 | Wang |
| 2014/0052241 A1 | 2/2014 | Harks |
| 2014/0057730 A1 | 2/2014 | Steinhauser |
| 2014/0057731 A1 | 2/2014 | Stephens |
| 2014/0057732 A1 | 2/2014 | Gilbert |
| 2014/0057733 A1 | 2/2014 | Yamamoto |
| 2014/0057734 A1 | 2/2014 | Lu |
| 2014/0057735 A1 | 2/2014 | Yu |

(56) References Cited

U.S. PATENT DOCUMENTS

| | | |
|---|---|---|
| 2014/0057736 A1 | 2/2014 | Burnett |
| 2014/0057737 A1 | 2/2014 | Solheim |
| 2014/0057738 A1 | 2/2014 | Albertsen |
| 2014/0057739 A1 | 2/2014 | Stites |
| 2014/0067050 A1 | 3/2014 | Costello |
| 2014/0074151 A1 | 3/2014 | Tischler |
| 2014/0081308 A1 | 3/2014 | Wondka et al. |
| 2014/0081375 A1 | 3/2014 | Bardill et al. |
| 2014/0088696 A1 | 3/2014 | Figulla |
| 2014/0114340 A1 | 4/2014 | Zhou |
| 2014/0128963 A1 | 5/2014 | Quill |
| 2014/0134322 A1 | 5/2014 | Larsen |
| 2014/0135817 A1 | 5/2014 | Tischler |
| 2014/0135907 A1 | 5/2014 | Gallagher |
| 2014/0142612 A1 | 5/2014 | Li |
| 2014/0142680 A1 | 5/2014 | Laske |
| 2014/0142688 A1 | 5/2014 | Duffy |
| 2014/0142691 A1 | 5/2014 | Pouletty |
| 2014/0163668 A1 | 6/2014 | Rafiee |
| 2014/0172076 A1 | 6/2014 | Jonsson |
| 2014/0172083 A1 | 6/2014 | Bruchman |
| 2014/0180397 A1 | 6/2014 | Gerberding |
| 2014/0180401 A1 | 6/2014 | Quill |
| 2014/0188157 A1 | 7/2014 | Clark |
| 2014/0194979 A1 | 7/2014 | Seguin |
| 2014/0222140 A1 | 8/2014 | Schreck |
| 2014/0228944 A1 | 8/2014 | Paniagua |
| 2014/0236288 A1 | 8/2014 | Lambrecht |
| 2014/0243954 A1 | 8/2014 | Shannon |
| 2014/0243967 A1 | 8/2014 | Salahieh |
| 2014/0243969 A1 | 8/2014 | Venkatasubramanian |
| 2014/0249564 A1 | 9/2014 | Daly |
| 2014/0249621 A1 | 9/2014 | Eidenschink |
| 2014/0257467 A1 | 9/2014 | Lane |
| 2014/0276395 A1 | 9/2014 | Wilson |
| 2014/0277074 A1 | 9/2014 | Kaplan |
| 2014/0277119 A1 | 9/2014 | Akpinar |
| 2014/0277388 A1 | 9/2014 | Skemp |
| 2014/0277389 A1 | 9/2014 | Braido |
| 2014/0277408 A1 | 9/2014 | Folan |
| 2014/0277411 A1 | 9/2014 | Börtlein |
| 2014/0277417 A1 | 9/2014 | Schraut |
| 2014/0277422 A1 | 9/2014 | Ratz |
| 2014/0277424 A1 | 9/2014 | Oslund |
| 2014/0277425 A1 | 9/2014 | Dakin |
| 2014/0277426 A1 | 9/2014 | Dakin |
| 2014/0288634 A1 | 9/2014 | Shalev |
| 2014/0288639 A1 | 9/2014 | Gainor |
| 2014/0296909 A1 | 10/2014 | Heipl |
| 2014/0296969 A1 | 10/2014 | Tegels |
| 2014/0296970 A1 | 10/2014 | Ekvall |
| 2014/0296975 A1 | 10/2014 | Tegels |
| 2014/0309727 A1 | 10/2014 | Lamelas |
| 2014/0330366 A1 | 11/2014 | Dehdashtian |
| 2014/0330368 A1 | 11/2014 | Gloss |
| 2014/0330369 A1 | 11/2014 | Matheny |
| 2014/0330370 A1 | 11/2014 | Matheny |
| 2014/0331475 A1 | 11/2014 | Duffy et al. |
| 2014/0343665 A1 | 11/2014 | Straubinger |
| 2014/0343669 A1 | 11/2014 | Lane |
| 2014/0343670 A1 | 11/2014 | Bakis |
| 2014/0358224 A1 | 12/2014 | Tegels |
| 2014/0371844 A1 | 12/2014 | Dale |
| 2014/0379020 A1 | 12/2014 | Campbell |
| 2015/0005857 A1 | 1/2015 | Kern |
| 2015/0018933 A1 | 1/2015 | Yang |
| 2015/0025621 A1 | 1/2015 | Costello |
| 2015/0025625 A1 | 1/2015 | Rylski |
| 2015/0039081 A1 | 2/2015 | Costello |
| 2015/0039083 A1 | 2/2015 | Rafiee |
| 2015/0066138 A1 | 3/2015 | Alexander |
| 2015/0066141 A1 | 3/2015 | Braido |
| 2015/0073548 A1 | 3/2015 | Matheny |
| 2015/0088248 A1 | 3/2015 | Scorsin |
| 2015/0088251 A1 | 3/2015 | May-Newman |
| 2015/0094802 A1 | 4/2015 | Buchbinder |
| 2015/0094804 A1 | 4/2015 | Bonhoeffer |
| 2015/0112428 A1 | 4/2015 | Daly |
| 2015/0112430 A1 | 4/2015 | Creaven |
| 2015/0119974 A1 | 4/2015 | Rothstein |
| 2015/0119978 A1 | 4/2015 | Tegels |
| 2015/0119980 A1 | 4/2015 | Beith |
| 2015/0119982 A1 | 4/2015 | Quill |
| 2015/0127032 A1 | 5/2015 | Lentz |
| 2015/0127093 A1 | 5/2015 | Hosmer |
| 2015/0127097 A1 | 5/2015 | Neumann |
| 2015/0127100 A1 | 5/2015 | Braido |
| 2015/0134054 A1 | 5/2015 | Morrissey |
| 2015/0142103 A1 | 5/2015 | Vidlund |
| 2015/0142104 A1 | 5/2015 | Braido |
| 2015/0148731 A1 | 5/2015 | McNamara |
| 2015/0150678 A1 | 6/2015 | Brecker |
| 2015/0157455 A1 | 6/2015 | Hoang |
| 2015/0157458 A1 | 6/2015 | Thambar |
| 2015/0173770 A1 | 6/2015 | Warner |
| 2015/0173897 A1 | 6/2015 | Raanani |
| 2015/0173898 A1 | 6/2015 | Drasler |
| 2015/0173899 A1 | 6/2015 | Braido |
| 2015/0196300 A1 | 7/2015 | Tischler |
| 2015/0196390 A1 | 7/2015 | Ma |
| 2015/0196393 A1 | 7/2015 | Vidlund |
| 2015/0209140 A1 | 7/2015 | Bell |
| 2015/0209143 A1 | 7/2015 | Duffy |
| 2015/0223729 A1 | 8/2015 | Balachandran |
| 2015/0223820 A1 | 8/2015 | Olson |
| 2015/0223934 A1 | 8/2015 | Vidlund |
| 2015/0230921 A1 | 8/2015 | Chau |
| 2015/0238312 A1 | 8/2015 | Lashinski |
| 2015/0238313 A1 | 8/2015 | Spence |
| 2015/0257879 A1 | 9/2015 | Bortlein |
| 2015/0257880 A1 | 9/2015 | Bortlein |
| 2015/0257881 A1 | 9/2015 | Bortlein |
| 2015/0257882 A1 | 9/2015 | Bortlein |
| 2015/0265402 A1 | 9/2015 | Centola |
| 2015/0265404 A1 | 9/2015 | Rankin |
| 2015/0272730 A1 | 10/2015 | Melnick |
| 2015/0272731 A1 | 10/2015 | Racchini |
| 2015/0272738 A1 | 10/2015 | Sievers |
| 2015/0282931 A1 | 10/2015 | Brunnett |
| 2015/0282958 A1 | 10/2015 | Centola |
| 2015/0289972 A1 | 10/2015 | Yang |
| 2015/0289974 A1 | 10/2015 | Matheny |
| 2015/0289977 A1 | 10/2015 | Kovalsky |
| 2015/0290007 A1 | 10/2015 | Aggerholm |
| 2015/0297346 A1 | 10/2015 | Duffy |
| 2015/0297381 A1 | 10/2015 | Essinger |
| 2015/0305860 A1 | 10/2015 | Wang |
| 2015/0305861 A1 | 10/2015 | Annest |
| 2015/0313710 A1 | 11/2015 | Eberhardt |
| 2015/0313712 A1 | 11/2015 | Carpentier |
| 2015/0320552 A1 | 11/2015 | Letac |
| 2015/0320556 A1 | 11/2015 | Levi |
| 2015/0327995 A1 | 11/2015 | Morin |
| 2015/0327996 A1 | 11/2015 | Fahim |
| 2015/0327999 A1 | 11/2015 | Board |
| 2015/0335422 A1 | 11/2015 | Straka |
| 2015/0342718 A1 | 12/2015 | Weber |
| 2015/0342734 A1 | 12/2015 | Braido |
| 2015/0351735 A1 | 12/2015 | Keranen |
| 2015/0351904 A1 | 12/2015 | Cooper |
| 2015/0351905 A1 | 12/2015 | Benson |
| 2015/0359628 A1 | 12/2015 | Keranen |
| 2015/0359629 A1 | 12/2015 | Ganesan |
| 2015/0366665 A1 | 12/2015 | Lombardi |
| 2015/0366667 A1 | 12/2015 | Bailey |
| 2015/0366690 A1 | 12/2015 | Lumauig |
| 2015/0374490 A1 | 12/2015 | Alkhatib |
| 2015/0374906 A1 | 12/2015 | Forsell |
| 2016/0000559 A1 | 1/2016 | Chen |
| 2016/0000562 A1 | 1/2016 | Siegel |
| 2016/0008128 A1 | 1/2016 | Squara |
| 2016/0008131 A1 | 1/2016 | Christianson |
| 2016/0015512 A1 | 1/2016 | Zhang |
| 2016/0015515 A1 | 1/2016 | Lashinski |

(56) References Cited

U.S. PATENT DOCUMENTS

| | | |
|---|---|---|
| 2016/0022417 A1 | 1/2016 | Karapetian |
| 2016/0022418 A1 | 1/2016 | Salahieh |
| 2016/0030165 A1 | 2/2016 | Mitra |
| 2016/0030168 A1 | 2/2016 | Spenser |
| 2016/0030169 A1 | 2/2016 | Shahriari |
| 2016/0030170 A1 | 2/2016 | Alkhatib |
| 2016/0030171 A1 | 2/2016 | Quijano |
| 2016/0030173 A1 | 2/2016 | Cai |
| 2016/0030175 A1 | 2/2016 | Madjarov |
| 2016/0038283 A1 | 2/2016 | Divekar |
| 2016/0045306 A1 | 2/2016 | Agrawal |
| 2016/0045308 A1 | 2/2016 | Macoviak |
| 2016/0045309 A1 | 2/2016 | Valdez |
| 2016/0045310 A1 | 2/2016 | Alkhatib |
| 2016/0045311 A1 | 2/2016 | McCann |
| 2016/0051358 A1 | 2/2016 | Sutton |
| 2016/0051362 A1 | 2/2016 | Cooper |
| 2016/0051364 A1 | 2/2016 | Cunningham |
| 2016/0066922 A1 | 3/2016 | Bridgeman |
| 2016/0067038 A1 | 3/2016 | Park |
| 2016/0067041 A1 | 3/2016 | Alkhatib |
| 2016/0074161 A1 | 3/2016 | Bennett |
| 2016/0074164 A1 | 3/2016 | Naor |
| 2016/0074165 A1 | 3/2016 | Spence |
| 2016/0081799 A1 | 3/2016 | Leo |
| 2016/0089234 A1 | 3/2016 | Gifford, III |
| 2016/0089235 A1 | 3/2016 | Yellin |
| 2016/0089236 A1 | 3/2016 | Kovalsky |
| 2016/0095700 A1 | 4/2016 | Righini |
| 2016/0095701 A1 | 4/2016 | Dale |
| 2016/0095702 A1 | 4/2016 | Gainor |
| 2016/0095703 A1 | 4/2016 | Thomas |
| 2016/0095704 A1 | 4/2016 | Whitman |
| 2016/0100844 A1 | 4/2016 | Li |
| 2016/0100939 A1 | 4/2016 | Armstrong |
| 2016/0100941 A1 | 4/2016 | Czyscon |
| 2016/0100942 A1 | 4/2016 | Morrissey |
| 2016/0106539 A1 | 4/2016 | Buchbinder |
| 2016/0113764 A1 | 4/2016 | Sheahan |
| 2016/0113766 A1 | 4/2016 | Ganesan |
| 2016/0113767 A1 | 4/2016 | Miller |
| 2016/0113768 A1 | 4/2016 | Ganesan |
| 2016/0120642 A1 | 5/2016 | Shaolian |
| 2016/0120643 A1 | 5/2016 | Kupumbati |
| 2016/0120646 A1 | 5/2016 | Dwork |
| 2016/0135951 A1 | 5/2016 | Salahieh |
| 2016/0136412 A1 | 5/2016 | McKinnon et al. |
| 2016/0143730 A1 | 5/2016 | Kheradvar |
| 2016/0143731 A1 | 5/2016 | Backus |
| 2016/0143734 A1 | 5/2016 | Shaolian |
| 2016/0151155 A1 | 6/2016 | Lutter |
| 2016/0157998 A1 | 6/2016 | Bruchman |
| 2016/0157999 A1 | 6/2016 | Lane |
| 2016/0158001 A1 | 6/2016 | Wallace |
| 2016/0158004 A1 | 6/2016 | Kumar |
| 2016/0158007 A1 | 6/2016 | Centola |
| 2016/0158011 A1 | 6/2016 | De Canniere |
| 2016/0158013 A1 | 6/2016 | Carpentier |
| 2016/0166381 A1 | 6/2016 | Sugimoto |
| 2016/0166382 A1 | 6/2016 | Nguyen |
| 2016/0166384 A1 | 6/2016 | Olson |
| 2016/0175096 A1 | 6/2016 | Dienno |
| 2016/0193044 A1 | 7/2016 | Achiluzzi |
| 2016/0193045 A1 | 7/2016 | Pollak |
| 2016/0193047 A1 | 7/2016 | Delaloye |
| 2016/0199177 A1 | 7/2016 | Spence |
| 2016/0199178 A1 | 7/2016 | Venkatasubramanian |
| 2016/0199180 A1 | 7/2016 | Zeng |
| 2016/0199182 A1 | 7/2016 | Gorman, III |
| 2016/0213470 A1 | 7/2016 | Ahlberg |
| 2016/0220363 A1 | 8/2016 | Peter |
| 2016/0235525 A1 | 8/2016 | Rothstein |
| 2016/0235530 A1 | 8/2016 | Thomas |
| 2016/0235531 A1 | 8/2016 | Ciobanu |
| 2016/0250022 A1 | 9/2016 | Braido |
| 2016/0250051 A1 | 9/2016 | Lim |
| 2016/0256168 A1 | 9/2016 | Nielsen |
| 2016/0256270 A1 | 9/2016 | Folan |
| 2016/0262884 A1 | 9/2016 | Lombardi et al. |
| 2016/0270910 A1 | 9/2016 | Birmingham |
| 2016/0270911 A1 | 9/2016 | Ganesan |
| 2016/0278922 A1 | 9/2016 | Braido |
| 2016/0296323 A1 | 10/2016 | Wulfman |
| 2016/0296333 A1 | 10/2016 | Balachandran |
| 2016/0302920 A1 | 10/2016 | Al-Jilaihawi |
| 2016/0302921 A1 | 10/2016 | Gosal |
| 2016/0302922 A1 | 10/2016 | Keidar |
| 2016/0310268 A1 | 10/2016 | Oba |
| 2016/0324640 A1 | 11/2016 | Gifford, III |
| 2016/0331527 A1 | 11/2016 | Vidlund et al. |
| 2016/0331529 A1 | 11/2016 | Marchand |
| 2016/0346081 A1 | 12/2016 | Zeng |
| 2016/0361161 A1 | 12/2016 | Braido |
| 2016/0374790 A1 | 12/2016 | Jacinto |
| 2016/0374801 A1 | 12/2016 | Jimenez |
| 2016/0374802 A1 | 12/2016 | Levi |
| 2016/0374803 A1 | 12/2016 | Figulla |
| 2016/0374842 A1 | 12/2016 | Havel |
| 2017/0079781 A1 | 3/2017 | Lim |
| 2017/0079785 A1 | 3/2017 | Li |
| 2017/0079787 A1 | 3/2017 | Benson |
| 2017/0079790 A1 | 3/2017 | Vidlund |
| 2017/0086973 A1 | 3/2017 | Zeng |
| 2017/0095256 A1 | 4/2017 | Lindgren |
| 2017/0100241 A1 | 4/2017 | Modine |
| 2017/0105839 A1 | 4/2017 | Subramanian |
| 2017/0165066 A1 | 6/2017 | Rothstein |
| 2017/0172737 A1 | 6/2017 | Kuetting |
| 2017/0202525 A1 | 7/2017 | Piazza |
| 2017/0252191 A1 | 9/2017 | Pacetti |
| 2017/0281193 A1 | 10/2017 | Asirvatham |
| 2017/0348098 A1 | 12/2017 | Rowe |
| 2017/0360570 A1 | 12/2017 | Berndt et al. |
| 2018/0014830 A1 | 1/2018 | Neumann |
| 2018/0092744 A1 | 4/2018 | Von Oepen |
| 2018/0116843 A1 | 5/2018 | Schreck |
| 2018/0116848 A1 | 5/2018 | McHugo |
| 2018/0133012 A1 | 5/2018 | Nathe |
| 2018/0185184 A1* | 7/2018 | Christakis ............... A61F 2/95 |
| 2018/0193153 A1 | 7/2018 | Brenzel et al. |
| 2018/0206983 A1 | 7/2018 | Noe |
| 2018/0256329 A1 | 9/2018 | Chambers |
| 2018/0296335 A1 | 10/2018 | Miyashiro |
| 2018/0311039 A1 | 11/2018 | Cohen |
| 2018/0325664 A1 | 11/2018 | Gonda |
| 2018/0333102 A1 | 11/2018 | De Haan et al. |
| 2018/0360602 A1 | 12/2018 | Kumar |
| 2018/0369006 A1 | 12/2018 | Zhang |
| 2019/0099265 A1 | 4/2019 | Braido |
| 2019/0105088 A1 | 4/2019 | Peterson et al. |
| 2019/0151067 A1 | 5/2019 | Zucker |
| 2019/0201192 A1 | 7/2019 | Kruse |
| 2019/0224028 A1* | 7/2019 | Finn ..................... A61F 2/2427 |
| 2019/0247189 A1 | 8/2019 | Dale |
| 2019/0247190 A1 | 8/2019 | Nathe |
| 2019/0321530 A1 | 10/2019 | Cambronne |
| 2019/0321531 A1 | 10/2019 | Cambronne |
| 2019/0365534 A1 | 12/2019 | Kramer |
| 2019/0365538 A1 | 12/2019 | Chambers |
| 2020/0000592 A1 | 1/2020 | Lee |
| 2020/0030507 A1 | 1/2020 | Higgins |
| 2020/0069423 A1 | 3/2020 | Peterson |
| 2020/0100897 A1 | 4/2020 | McLean |
| 2020/0113682 A1 | 4/2020 | Chang |
| 2020/0129294 A1 | 4/2020 | Hariton |
| 2020/0155306 A1 | 5/2020 | Bonyuet |
| 2020/0163765 A1 | 5/2020 | Christianson |
| 2020/0179111 A1 | 6/2020 | Vidlund |
| 2020/0179115 A1 | 6/2020 | Chambers |
| 2020/0188101 A1 | 6/2020 | Chambers |
| 2020/0222179 A1 | 7/2020 | Chambers |
| 2020/0253733 A1 | 8/2020 | Subramanian |
| 2020/0261219 A1 | 8/2020 | Kumar |
| 2020/0276013 A1 | 9/2020 | Chambers |

(56) References Cited

U.S. PATENT DOCUMENTS

| | | |
|---|---|---|
| 2020/0315678 A1 | 10/2020 | Mazzio et al. |
| 2020/0337765 A1 | 10/2020 | Smith |
| 2020/0368023 A1 | 11/2020 | Kheradvar |
| 2020/0375733 A1 | 12/2020 | Diedering |
| 2021/0236274 A1 | 8/2021 | Benson |
| 2021/0236276 A1 | 8/2021 | Diedering |
| 2021/0275297 A1 | 9/2021 | Berndt |
| 2021/0275301 A1 | 9/2021 | Kumar |
| 2021/0290383 A1 | 9/2021 | Chambers |
| 2022/0031451 A1 | 2/2022 | Spence |
| 2022/0338979 A1 | 10/2022 | Benichou |
| 2023/0218397 A1 | 7/2023 | Chambers et al. |

FOREIGN PATENT DOCUMENTS

| | | |
|---|---|---|
| AU | 2013201970 B2 | 3/2016 |
| CN | 2820130 Y | 9/2006 |
| CN | 100413471 C | 8/2008 |
| CN | 100444811 C | 12/2008 |
| CN | 101953723 A | 1/2011 |
| CN | 101953724 A | 1/2011 |
| CN | 101953725 A | 1/2011 |
| CN | 101953728 A | 1/2011 |
| CN | 101953729 A | 1/2011 |
| CN | 101961269 A | 2/2011 |
| CN | 101961273 A | 2/2011 |
| CN | 102036622 | 4/2011 |
| CN | 201870772 U | 6/2011 |
| CN | 203290964 U | 11/2013 |
| CN | 103431931 A | 12/2013 |
| CN | 203379235 U | 1/2014 |
| CN | 103598939 A | 2/2014 |
| CN | 103610520 A | 3/2014 |
| CN | 203619728 U | 6/2014 |
| CN | 203677318 U | 7/2014 |
| CN | 104287804 A | 1/2015 |
| CN | 104352261 A | 2/2015 |
| CN | 204133530 U | 2/2015 |
| CN | 204181679 U | 3/2015 |
| CN | 204246182 U | 4/2015 |
| CN | 204318826 U | 5/2015 |
| CN | 104688292 A | 6/2015 |
| CN | 102985033 B | 8/2015 |
| CN | 204581598 U | 8/2015 |
| CN | 204581599 U | 8/2015 |
| CN | 204683686 U | 10/2015 |
| CN | 105596052 A | 5/2016 |
| CN | 105615936 A | 6/2016 |
| CN | 205286438 U | 6/2016 |
| CN | 108348270 | 7/2018 |
| CN | 107252363 B | 4/2020 |
| CN | 106913909 B | 9/2020 |
| CN | 107007887 B | 10/2020 |
| DE | 102010021345 A1 | 11/2011 |
| EP | 2596754 A1 | 5/2013 |
| EP | 2 810 620 A1 | 12/2014 |
| EP | 2967858 A2 | 1/2016 |
| EP | 2982336 A1 | 2/2016 |
| EP | 2967845 B1 | 8/2018 |
| EP | 2950752 B1 | 7/2022 |
| JP | 2016531722 A | 10/2016 |
| WO | WO1995016476 A1 | 6/1995 |
| WO | WO2009127973 A2 | 10/2009 |
| WO | WO2014210299 A1 | 12/2014 |
| WO | WO2015004173 A1 | 1/2015 |
| WO | WO2016100806 A1 | 6/2016 |

OTHER PUBLICATIONS

Notification Concerning Transmittal of International Preilminary Report on Patentability and International Preliminary Report on Patentability issued in PCT application No. PCT/US2019/049410, dated Mar. 18, 2021.
Extended Search Report issued by the European Patent Office for application No. 19857502.9, date of completion of search Apr. 20, 2022, 7 pages.
The Alta Valve™. Attributes, Challenges, and Future Programs, Dr. Philippe Genereux, MD, Jun. 22, 2018, 15 pages.
4C Medical's Alta Valve: The First-in-Human Experience, Joep Rodes-Cabau, MD, Sep. 21, 2018, 43 pages, 80 pages, and 16 pages.
Ferreira-Neto et al., "Transcatheter Mitral Valve Replacement With a New Supra-Annular Valve-First-in-Human Experience with the AltaValve System," https://doi.org/10.1016/j.jcin.2018.10.056, By The American College of Cardiology Foundation Published by Elsevier, Jan. 28, 2019.
European Office Action in Application No. 19857502.9, dated Jun. 5, 2022, 7 pages.
Indian Office Action in Application No. 202137014456, dated Dec. 6, 2022, 7 pages.
Japanese Office Action in Application No. 2021-512383, dated Aug. 17, 2021, 8 pages.
Japanese Office Action in Application No. 2021-512383, dated Apr. 7, 2022, 4 pages.
Japanese Decision of Rejection in Application No. 2021-512383, dated Jan. 4, 2023, 6 pages.
Taiwanese Office Action in Application No. 108131952, dated Oct. 6, 2022, 10 pages.
International Search Report and Written Opinion in Application No. PCT/US2019/049410, dated Dec. 13, 2019, 12 pages.
Chinese Office Action in Application No. 2019800729970.2, dated Jul. 21, 2023, 9 pages.

\* cited by examiner

STENT LOADING DEVICE

CROSS-REFERENCE TO RELATED APPLICATIONS

This application claims the benefit of U.S. Provisional Application Ser. No. 62/726,602, filed Sep. 4, 2018 and entitled FUNNELING LOADING DEVICE FOR STENT, the entire contents of which are incorporated herein by reference.

STATEMENT REGARDING FEDERALLY SPONSORED RESEARCH OR DEVELOPMENT

Not Applicable

BACKGROUND OF THE INVENTION

Field of the Invention

The invention relates to devices and methods for implanting devices within a heart chamber. More specifically, the invention relates to devices configured to load a stent, e.g., a prosthetic heart valve frame, into a lumen of a delivery sheath or catheter for translation through the lumen to the distal end of the delivery sheath or catheter.

Description of the Related Art

Stents in general, and prosthetic cardiac valve and left atrial appendage occluding devices specifically, are well known in the art. The native heart valves, e.g., aortic, pulmonary, tricuspid and mitral valves, are critical in assuring the forward-only flow of an adequate supply of blood through the cardiovascular system. These heart valves may lose functionality as a result of, inter alia, congenital, inflammatory, infectious diseases or conditions. Early interventions repaired or replaced the dysfunctional valve(s) during open heart surgery. More recently, besides the open heart surgical approach discussed above, gaining access to the valve of interest may be achieved percutaneously via one of at least the following known access routes: transapical; transfemoral; transatrial; and trans septal delivery techniques, collectively transcatheter techniques.

Generally, in a transcatheter technique, the prosthetic valve is mounted within a stented frame that is capable of achieving collapsed and expanded states. The device is collapsed and advanced through a sheath or delivery catheter positioned in a blood vessel of the patient until reaching the implantation site. The stented frame is generally released from the catheter or sheath and, by a variety of means, expanded with the valve to the expanded functional size and orientation within the heart. One of the key issues is ease of delivery of the prosthetic valve, including the stent frame and valve. More specifically the outer diameter of the collapsed device within the catheter is of significant interest. The present invention addresses this issue.

DESCRIPTION OF THE RELATED ART

The human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve. See generally FIG. 1.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood into the chamber it just flowed out of. For example, the mitral valve when working properly provides a one-way valving between the left atrium and the left ventricle, opening to allow antegrade flow from the left atrium to the left ventricle and closing to prevent retrograde flow from the left ventricle into the left atrium. This retrograde flow, when present, is known as mitral regurgitation or mitral valve regurgitation.

Native heart valves may be, or become, dysfunctional for a variety of reasons and/or conditions including but not limited to disease, trauma, congenital malformations, and aging. These types of conditions may cause the valve structure to fail to close properly resulting in regurgitant retrograde flow of blood from the left ventricle to the left atrium in the case of a mitral valve failure.

Mitral valve regurgitation is a specific problem resulting from a dysfunctional mitral valve that allows at least some retrograde blood flow back into the left atrium from the right atrium. In some cases, the dysfunction results from mitral valve leaflet(s) that prolapse up into the left atrial chamber, i.e., above the upper surface of the annulus instead of connecting or coapting to block retrograde flow. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

Regurgitation can be a problem with native heart valves generally, including tricuspid, aortic and pulmonary valves as well as mitral valves.

Native heart valves generally, e.g., mitral valves, therefore, may require functional repair and/or assistance, including a partial or complete replacement. Such intervention may take several forms including open heart surgery and open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally-adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access routes: transapical; transfemoral; transatrial; and trans septal delivery techniques.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See, e.g., U.S. Pat. No. 8,852,271 (Murray, III); U.S. Pat. No. 8,747,459 (Nguyen); U.S. Pat. No. 8,814,931 (Wang); U.S. Pat. No. 9,402,720 (Richter); U.S. Pat. No. 8,986,372 (Murray, III); and U.S. Pat. No. 9,277,991 (Salahieh); and U.S. Pat. Pub. Nos. 2015/0272731 (Racchini); and 2016/0235531 (Ciobanu).

In addition, known "replacement" prosthetic heart valves are intended for full replacement of the native heart valve. Therefore, these replacement heart valves physically engage tissue within the annular throat, i.e., below the annular plane and upper annular surface, and/or valve leaflets, thereby eliminating all remaining functionality of the native valve and making the patient completely reliant on the replacement valve. Generally speaking, it is a preferred solution that maintains and/or retains the native function of a heart valve, thus supplementation of the valve is preferred rather than full replacement. Obviously, there will be cases when native valve has either lost virtually complete functionality before the interventional implantation procedure, or the native valve continues to lose functionality after the implantation procedure. The preferred solution is delivery and implantation of a valve device that will function both as an adjunctive and/or supplementary functional valve as well as be fully capable of replacing the native function of a valve that has lost, or will lose, most or all of its functionality. However, the inventive solutions described infra will apply generally to all types and forms of heart valve devices, unless otherwise specified. The present disclosure also applies, as the skilled artisan will recognize, to stents generally.

Further, known solutions for, e.g., the mitral valve replacement systems, devices and methods require 2-chamber solutions, i.e., there is involvement and engagement of the implanted replacement valve device in the left atrium and the left ventricle. Generally, these solutions include a radially expanding stent in the left atrium, with anchoring or tethering (disposed downward through the native annulus or annular throat) connected from the stent device down through the annular throat, with the sub-annular surface within the left ventricle, the left ventricular chordae tendineae and even into the left ventricle wall surface(s). See, e.g., the MitraClip® marketed by the Abbott Group and currently the only US approved repair device. With the MitraClip® a catheter containing the MitraClip® is inserted into the femoral vein. The device enters the heart through the inferior vena cava to the right atrium and delivered transseptally. The MitraClip® passes through the annulus into the left ventricle and sits below the leaflets, clipping the leaflets to decrease regurgitation.

Such 2-chamber and native annulus solutions are unnecessary bulky and therefore more difficult to deliver and to position/recapture/reposition from a strictly structural perspective. Further, the 2-chamber solutions present difficulties in terms of making the ventricular anchoring and/or tethering connections required to hold position. Moreover, these solutions interfere with the native valve functionality as described above because the device portions that are disposed within the left ventricle must be routed through the native annulus and/or annular throat and native mitral valve, thereby disrupting any remaining coaptation capability of the native leaflets. In addition, the 2-chamber solutions generally require an invasive anchoring of some of the native tissue, resulting in unnecessary trauma and potential complication.

It will be further recognized that the 2-chamber mitral valve solutions require sub-annular and/or ventricular engagement with anchors, tethers and the like precisely because the atrial portion of the device fails to adequately anchor itself to the atrial chamber and/or upper portion of the annulus. Again, some of the embodiments, or portions thereof, described herein are readily applicable to single or 2-chamber solutions, unless otherwise indicated.

Finally, known prosthetic cardiac valves consist of two or three leaflets that are arranged to act as a one-way valve, permitting fluid flow therethrough in the antegrade direction while preventing retrograde flow. The native mitral valve is located retrosternally at the fourth costal cartilage, consisting of an anterior and posterior leaflet, chordae tendinae, papillary muscles, ventricular wall and annulus connected to the atria. Each native leaflet is supported by chordae tendinae that are attached to papillary muscles which become taut with each ventricular contraction preserving valvular competence. Both the anterior and posterior leaflets of the native valve are attached via primary, secondary and tertiary chordae to both the antero-lateral and posterio-medial papillary muscles. A disruption in either papillary muscle in the setting of myocardial injury, can result in dysfunction of either the anterior or posterior leaflet of the mitral valve. Other mechanisms may result in failure of one, or both of the native mitral leaflets. In the case of a single mitral valve leaflet failure, the regurgitation may take the form of a non-central, eccentric jet of blood back into the left atrium. Other leaflet failures may comprise a more centralized regurgitation jet. Known prosthetic valve replacements generally comprise leaflets which are arranged to mimic the native valve structure, which may over time become susceptible to similar regurgitation outcomes.

The applications for collapsible and expandable stents are not limited to prosthetic heart valve implants. Vascular stents are commonly used and are generally collapsible to facilitate delivery through the lumen of a delivery catheter to the working site where the stent is translated out of the lumen of the catheter and it is expanded, either by a self-expanding means or through an expanding mechanism such as, inter alia, an expandable balloon.

As discussed above, known delivery methods and devices comprise expandable prosthetic valve stents and vascular stents that are collapsed during delivery via a delivery catheter. The problems with such collapsing and expanding structures include placing strain on the regions of the structure, e.g., stent, that must bend to accommodate the collapsing and expanding states. Further, the collapsed geometry in known devices may not be controlled or predictable, adding to the strain on the collapsing and expanding structure elements. Thus, the structures and methods for achieving the collapsed state within the delivery catheter or sheath lumen must allow predictable and repeatable collapsing to maintain and retain the integrity of the collapsing structure. Moreover, the stent, e.g., prosthetic heart valve or vascular stent, may comprise biological and/or biologically compatible material that cannot be allowed to become dry. Therefore, retaining a fluid reservoir within which the subject stent may reside is critical.

Various embodiments of the present invention address these, inter alia, issues.

BRIEF SUMMARY OF THE INVENTION

A device and method for predictably and controlling the collapsing of a collapsible and expandable stent for subsequent translation through a delivery sheath lumen to an anatomical target such as a heart valve or intravascular location for expansion and implantation. The loading device defines in inner lumen comprising a successively decreasing, from the proximal to the distal direction, inner diameter to a region of constant inner diameter wherein the stent is in a collapsed configuration. The device and method may provide for an at least partially collapsed configuration of the stent that may be further collapsed as a part of the implantation procedure and may comprise a stent that is pre-loaded for future use.

DETAILED DESCRIPTION OF THE INVENTION

Generally, various embodiments of the present invention are directed to devices and methods for achieving a predictable collapsed configuration or state for a collapsible and expandable support structure or stent as well as providing a mechanism for ensuring moisture retention within biological materials that may be attached or otherwise integrated with the collapsible and expandable support structure during the collapsing step.

The support structure or stent has multiple functions to aid with the treatment of cardiac valve regurgitation (mitral or tricuspid). These functions include its function as a scaffold for the functioning 4C valve, apposition to the atrial anatomy, optimized radial force for compliance with atrial distension, ability to load and deploy from a minimally invasive delivery system, and geometry to support with mitigating against paravalvular leak (PVL). The design features of the stent are adapted to meet one or more of the functions identified above. Specific design features and attributes for exemplary stents are discussed in detail below to assist in understanding of the utility of the funneling loading device and related methods. As discussed above, the invention is not limited to prosthetic heart valves comprising stent support structures, but may also be applied to collapsible and expandable stents such as commonly used for intravascular procedures.

Certain exemplary embodiment stent design concepts are intended to support minimally invasive procedures for the treatment of valvular regurgitation—mitral, tricuspid and/or otherwise. The stents may be self-expandable (e.g. nitinol or similar materials) or balloon expandable (e.g. cobalt chromium or similar materials). The stents are typically made of cells that may be open celled diamond like structures or continuous structures that have a working cell element. The stents may also be constructed using tubing, wires, braids or similar structures. Specific design features that aid with the functioning of the stent are described in detail below.

Stent "Iris" Transition Cells

Figure 1:
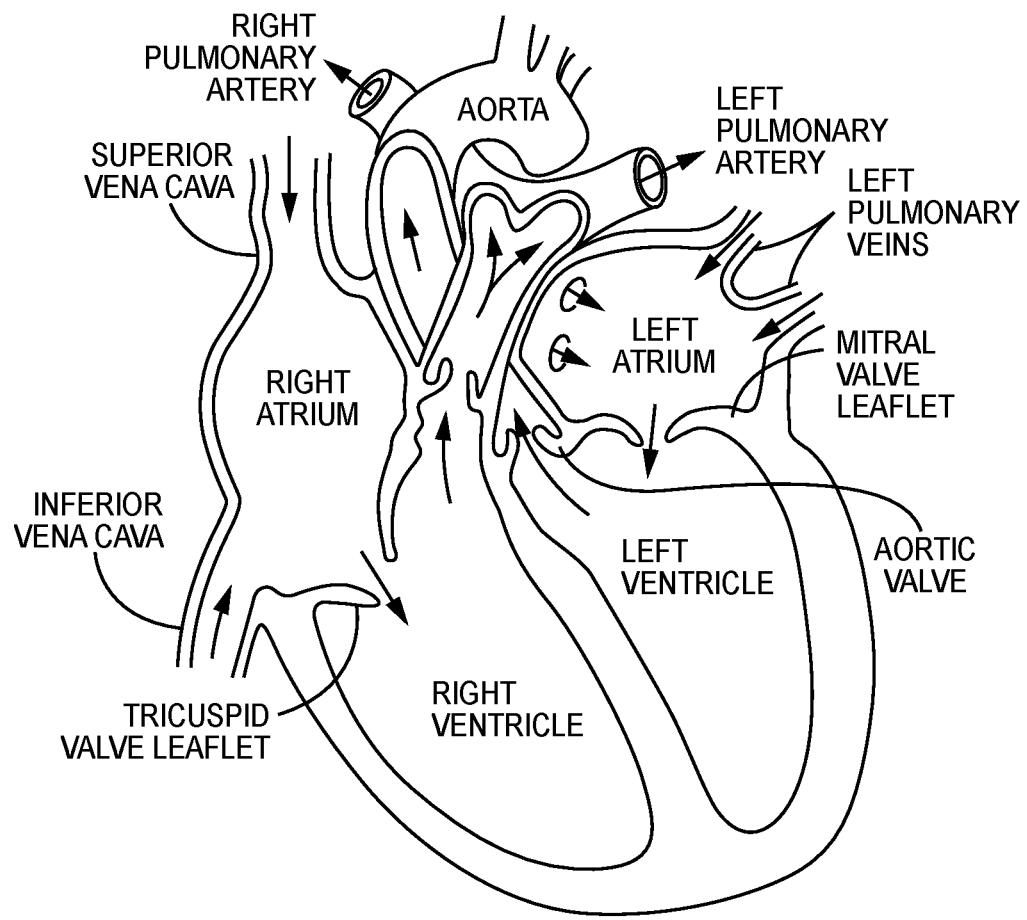
FIG. 1 illustrates certain features of the heart in cross-section.
Figure 2:
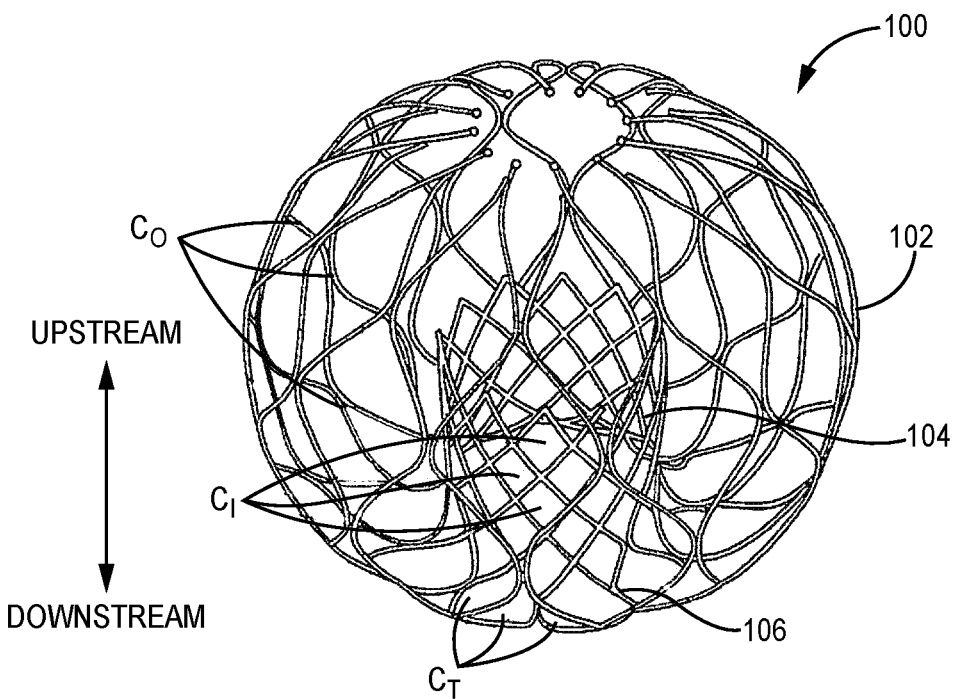
FIG. 2 illustrates a perspective view of an exemplary stent.
Figure 3A:
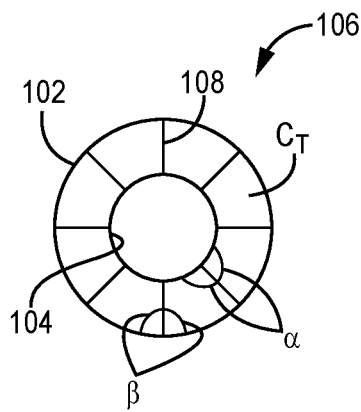
FIG. 3A illustrates a bottom view of one embodiment of a transition section of the exemplary stent of FIG. 2.
Figure 3B:
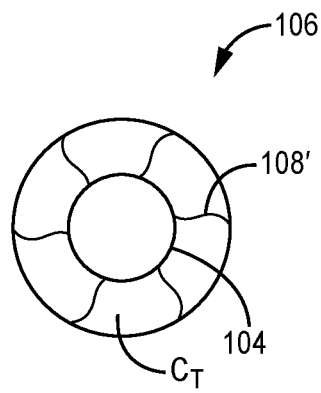
FIG. 3B illustrates a bottom view of one embodiment of a transition section of the exemplary stent of FIG. 2.

With reference now to FIGS. 2-3B, one embodiment of the stent 100 of the present invention comprises an outer section 102—that may generally be circular though need not be a perfectly round circular structure when fully and/or partially expanded—and an inner valve support section 104—which may be cylindrical but need not be a constant diameter cylinder and is adapted to support and retain prosthetic valve leaflets (not shown in FIG. 2) within the inner valve support section 104, most preferably at a point that located above the native annulus, e.g., the mitral valve annulus, though other attachment points for the prosthetic leaflets are within the scope of the present invention. Further, as discussed above, the stent 100 may be configured to supplement and/or replace the function of the tricuspid valve. A preferred construction comprises the prosthetic leaflets disposed above the native leaflets, wherein the prosthetic leaflets are attached and spaced sufficiently away from (above) the native leaflets so as to not physically interfere or interact with the native leaflets. However, certain embodiments contemplate some interaction with the native leaflets.

Individual cells $C_O$ forming the outer section 102 of stent 100 are visible in FIG. 2 as open cell regions defined by the material used to form the expandable stent 100.

Individual cells $C_I$ forming the inner valve support section 104 are also illustrated as open cells regions formed within an inner region R defined by outer section 102, wherein the inner valve support section extends radially upward into the inner region R. As shown, individual cells $C_I$ are of a different size, and may comprise a different shape, than that of individual cells $C_O$.

The region of stent 100 that facilitates the radially inward transition of the stent 100 from the outer section 102 to the inner section 104 of the stent 100 is the transition cell region 106. Transition cell region 106 may comprise cells $C_T$ that may comprise a different size and/or shape that either the outer section cells $C_O$ and/or the inner section cells $C_I$. The outer and/or inner regions 102, 104, and/or transition cell region 106 of the stent 100 may be constructed from one continuous structure or may combine two or more structures to achieve intended design goals. Transition cell region 106 comprises generally a radially upward turn to allow the inner valve support section 104 to reside within the inner region 102 as shown in FIG. 2. In some embodiments, the lower portion of inner valve support section 104, that is the portion of the inner valve support section 104 that is in connection with the cells $C_T$ of transition cell region 106 may also comprise a curving shape to facilitate and/or complete the radially upward turn into the inner region 102.

The geometry and/or shape of the transition cells $C_T$ may be substantially straight segments when expanded as in FIG. 3A below or may, as shown in FIG. 3B, incorporate an offset or a twist in the stent cell pattern when expanded to allow for a controlled compression of the stent. Exemplary cross-sectional geometry of the transition cell region 106 viewed from the bottom of stent 100 is represented schematically in FIGS. 3A and 3B.

This transition cell region 106 of the stent 100 may be a strut, completed cell section or a partial cell section. The transition cell region 106 may have any number of struts (minimum of 3) or cell sections as generally required to meet design needs. Transition cells $C_T$ or struts may be evenly spaced and formed by substantially straight and equally spaced apart struts 108 as shown in FIG. 3A, that extend away from the inner valve support section 104 with equal angles α on both sides of the strut 108 and equal angles β on both sides of strut 108 with respect to its intersection or integration with outer support section 102.

Figure 3C:
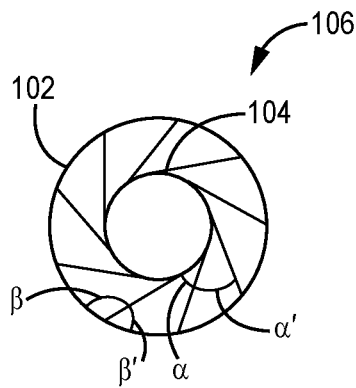
FIG. 3C illustrates a bottom view of one embodiment of a transition section of the exemplary stent of FIG. 2.

In a preferred embodiment, the struts 108 of transition section 106 may be straight as in FIG. 3A, but with non-equal angles relative to the inner valve support section 104 and outer support section 102 as shown in FIG. 3C. There, the straight struts 108 are slanted so that a smaller angle α and a larger angle α' are provided relative to the inner valve support section 104. Similarly, a smaller angle β' and a larger angle β are provided relative to the outer support section 102. This allows a compressed nesting of the slanted struts 108 of transition section 106.

In another preferred embodiment, the transition cell region 106 may comprise transition cell struts 108' that comprise transition cells CT that are formed by struts 108' having an offset, i.e., not straight, are twisted and/or curvilinear. The degree of offset and/or twist and/or curvature of the struts 108', and therefore the size and/or shape of the resultant expanded cells CT may be varied dependent on the number of cells/struts in the transition cell region 106, packing density when the stent is collapsed, and stress/strain distribution limitations of the transition cell region 106.

Figure 4A:
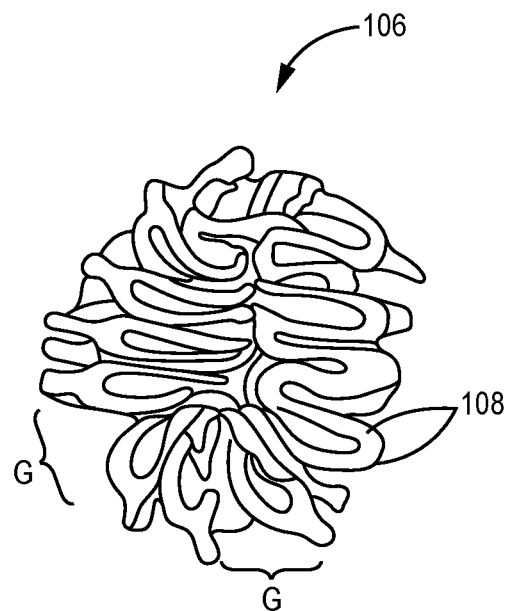
FIG. 4A illustrates a bottom view of one embodiment of a collapsed transition section of the exemplary stent of FIG. 2.

The structure of FIGS. 3B and 3C are preferred over the straight transition cell region 106 structure of FIG. 3A for several reasons. FIG. 4A shows a transition cell region 106 in a collapsed form using the substantially straight struts 108 of FIG. 3A and with, undesirable, gaps G between selected struts 108. Though this resultant gapping collapsed transitional cell region 106 is workable, it is not optimal.

Figure 4B:
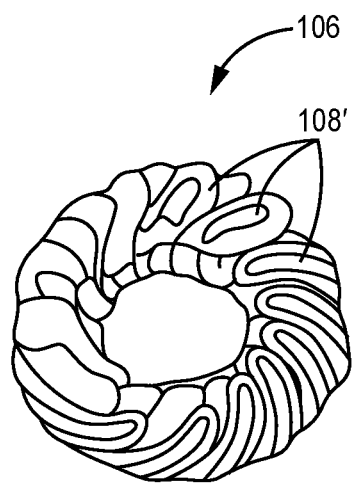
FIG. 4B illustrates a bottom view of one embodiment of a collapsed transition section of the exemplary stent of FIG. 2.

Thus, the transition section 106 of FIG. 4B, using e.g., the offset and/or twisted and/or curved plurality of struts 108' of FIG. 3B or the slanted straight struts 108 of FIG. 3C, allows for a controlled and predictable collapsed form of the stent, without gapping between the struts 108'. This, in turn, minimizes the amount of stress/strain concentration at the lower region of the stent 100 during collapsing as is required for delivery of the expandable stent 100 to the heart region of interest. Additionally, the collapse of the cells is also symmetrical and uniform, which could aid with mitigating against damage to the valve tissue or fabric when it is attached to the stent cells. Reduction in overall stress/strain of the transition strut section may benefit the durability of the stent and the valve tissue.

A feature of certain embodiments of the transition cell region 106 as shown in FIGS. 3B and 3C and 4B, i.e., with offset, twisted and/or curved struts 108' or slanted straight struts 108, is that, as best shown in FIG. 3B, the struts 108' each comprise the same offset, twist and/or curvature. This, in turn, enables a close nesting of adjacent struts 108' as the stent 100 is collapsed down for delivery and subsequent expansion. Thus, as the stent is collapsed for loading into a delivery system, the transition section design allows for a controlled compression of the stent, and reduces the stress concentration on the stent cells. of the transition strut section may benefit the durability of the stent and the valve tissue.

As the skilled artisan will now recognize from the above, the geometry of the exemplary stent's struts enables a transition from expanded to collapsed. The stent that may be collapsed using the following inventive embodiments is certainly not restricted to the exemplary cases described above. Any stent requiring collapsing from an expanded configuration to achieve a configuration that fits within the lumen of a delivery sheath may be collapsed with the present inventions.

Figure 5:
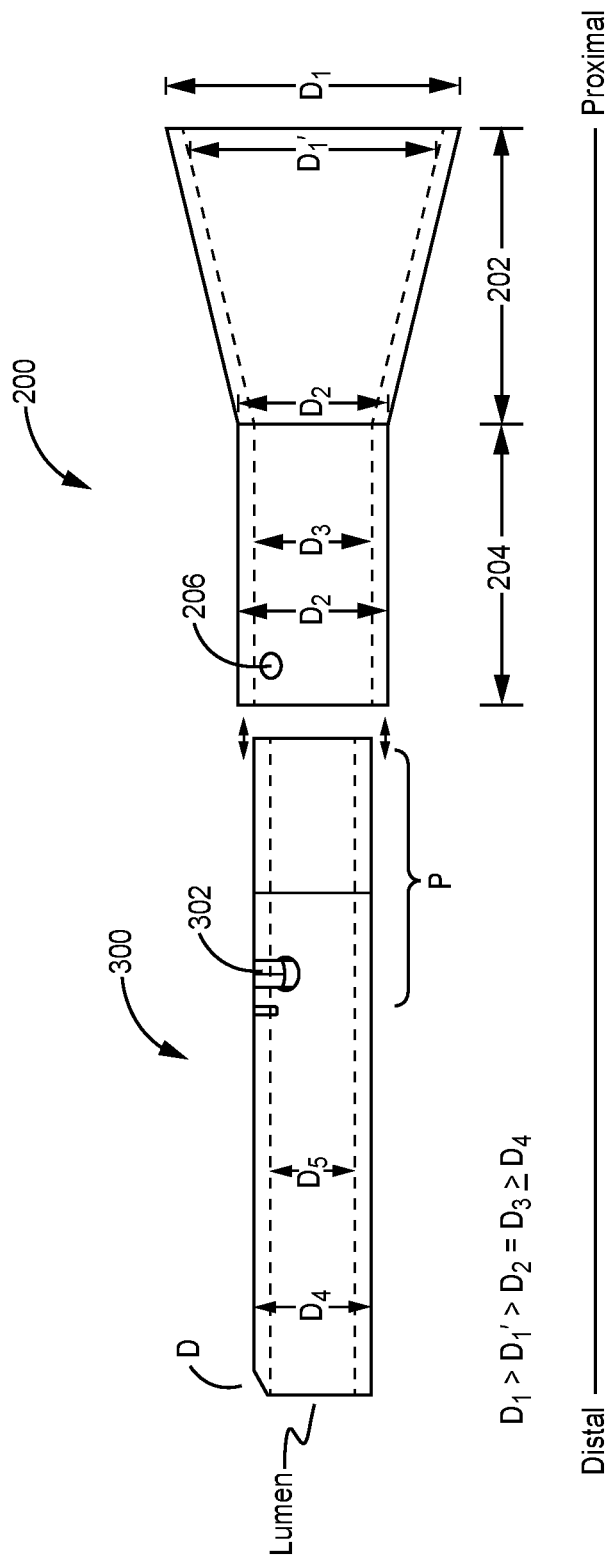
FIG. 5 illustrates a side broken away view of one embodiment of the present invention.

Thus, FIG. 5 illustrates an exemplary loading device 200 that may initiate the transition of the exemplary stent from expanded to collapsed, wherein the collapsed state or configuration is prepared and sufficient for translation into and along the delivery catheter or sheath to the targeted anatomical location.

FIG. 5 therefore illustrates a loading funnel 200 on the proximal side of the image with a sheath 300, which may comprise modifications to known delivery catheters as described herein. The loading funnel 200 and sheath 300 are illustrated as two separate elements that may be removably connected using known techniques. However, as the skilled artisan will recognize, the loading funnel 200 and sheath 300 may be preassembled and/or manufactured as an integrated unit in certain embodiments. The loading funnel 200 comprises a proximal decreasing diameter (from proximal to distal) section 202, illustrated as conical but in other embodiments may comprise a curvilinear and or concave profile. In each case, the dimensional requirement is that the inner diameter D1' of the proximal decreasing diameter section 202 comprises a lumen comprising a smoothly decreasing inner diameter moving from the proximal inner diameter D1' to the distal inner diameter D2. Thus, proximal decreasing diameter section 202 comprises a maximum inner diameter (shown as D1') at its proximal end and a minimum inner diameter at its distal end (shown as D2). And, as shown, proximal outer diameter D1 of proximal section 202 is greater than proximal inner diameter D1'.

The decreasing diameter proximal section 202 of loading funnel 200 transitions distally into a constant diameter section 204, comprising an inner diameter D3 that is substantially the same as the smallest inner diameter D2 of the decreasing diameter proximal section 202 at its distal end, the transition therebetween preferably smooth to facilitate stressless translation of the collapsing exemplary stent therealong.

Transitional sheath 300 comprises a proximal end portion P and a distal D end, an outer diameter D4 and defining a lumen comprising inner diameter D5, wherein both D4 and D5 are substantially constant. The lumen for each of devices 200 and 300 is shown in dashed lines in FIG. 5.

Outer diameter D4 of sheath 300 may be the same as, or smaller than, the inner diameter D3 of the constant diameter section 204 of loading funnel 200. Thus, as shown, the proximal end portion P of sheath 300 is adapted or configured to fit within at least a distal portion of the lumen of the constant diameter section 204 of the loading funnel 200 to create a lumen that is fluidly communicating from the proximal end of the loading sheath 200 to the distal end D of the sheath 300. Generally, and without limitation, the various relevant diameter relationships are as follows, using the nomenclature provided above and in FIG. 5:

$$D1 > D1' > D2 = D3 \geq D4$$

Sheath 300 may be removably connected with the constant diameter section 204 in a variety of ways, including but certainly not limited to: a frictional fit and/or the illustrated detent male member 206 disposed on constant diameter section 204 of loading funnel 200 until engaged, and pushed radially outwardly, by the proximal end portion P of sheath 300. Ultimately, when the male member 206 aligns with the slot or aperture 302, male member 206 may, as the skilled artisan will recognize, drop or snap within the receiving aperture 302 and/or slot as illustratively defined in the outer wall of constant diameter section 204 of sheath 300. In some cases, the slot 302 may allow relative rotation of the sheath 300 and loading funnel 200 within the slot 302, thus enabling relative rotation within the limits of the length of the slot 302 between the loading funnel 200 and the transitional sheath 300. As the skilled artisan will recognize, the above male member/slot or aperture arrangement may be effectively reversed: wherein the male member 206 may be disposed on the sheath 300 and the slot or aperture may be disposed on the constant diameter section 204 of loading funnel 200. Other possible connection alternatives, within limitation, between loading funnel 200 and sheath 300 may comprise a threaded connection; and a frictional fit. Still more alternatively, the components 200, 300 may be provided as a single unit, wherein the inner diameter of the single unit distal of the decreasing diameter section is constant. What is required in all cases is that the loading funnel 200 and sheath 300 are functionally connected to provide the dimensional features described above.

In some embodiments, the proximal end portion P of sheath 300 when engaged within constant diameter section 204 of loading funnel may extends proximally to the distal end of loading funnel 202, effectively sliding through the entire length of the lumen of constant diameter section 204. In other embodiments, proximal end portion P engages only a portion of the length of the lumen of constant diameter section 204.

The collapsing of an exemplary collapsible stent from an expanded configuration may be achieved by translating the expanded stent distally into the lumen of loading funnel 200 progressively along and through the decreasing diameter section 202, where the walls of loading funnel's lumen exert constant and equal pressure on the stent, causing a progressive, predictable and relatively stress-free collapsing and distal translation into the sheath 300 comprising lumen of inner diameter D5. At this stage, the exemplary stent is collapsed and ready for translation distally to the anatomical target. Release of the exemplary stent from the distal end of sheath 300 allows the stent, if self-expanding, to expand to its working expanded configuration. In other cases the stent may require additional assistance to expand, e.g., through push/pull wires and/or expanding balloons as is known in the art.

Figure 6:
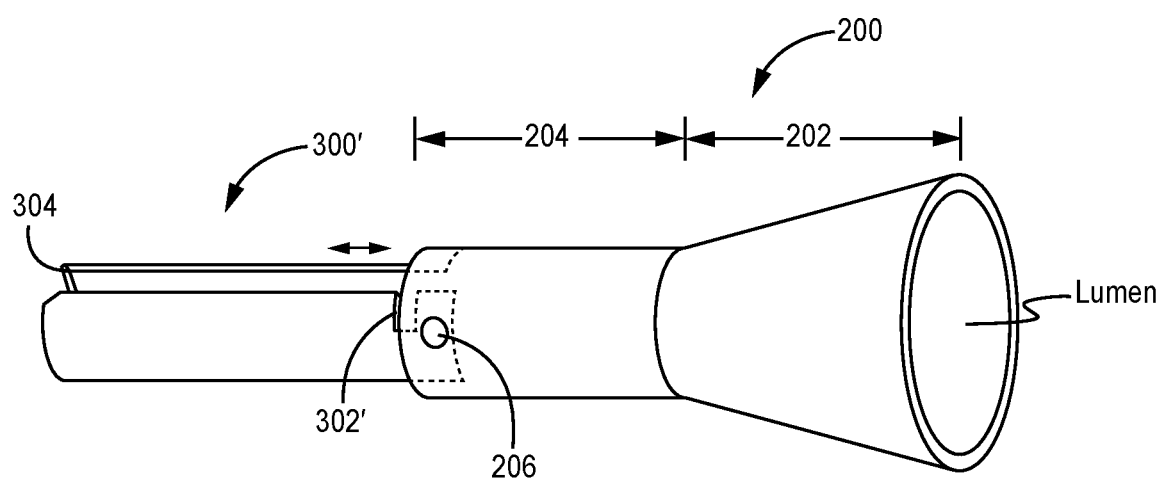
FIG. 6 illustrates a perspective view of one embodiment of the present invention.

FIG. 6 provides an alternative, clamshell type construction for the transitional sheath 300', wherein the transitional sheath 300' is formed from a planar sheet 304 that may have a precurved shape as illustrated. The loading funnel 200 is as described above in connection with FIG. 5.

As the planar sheet 304 is reduced in diameter to slidingly fit within the constant diameter section 204 of the loading funnel 200, and form sheath 300', the male member 206 described above located on loading funnel 200, may align with and fit within an aperture or slot 302' of transitional sheath 300' to provide a removable locking fit between transitional sheath 300' and loading funnel 200 as described above. As noted above in the embodiment of FIG. 5, male member 206 and aperture or slot 302' may reverse positions in the embodiment of FIG. 6. In the case of a 302', the loading funnel 200 may rotate relative to the sheath 300', as the male member 206 rotates within the slot 302'. In certain cases, the clamshell type sheath 300' of FIG. 6 may not reach complete closure along its length when reduced in diameter to fit within the constant diameter section 204 of transition sheath 300', thus leaving a longitudinal slot along the transitional sheath 300'. The male member 206 of constant diameter section 204 may be guided along this longitudinal slot to the radial slot 302' shown in FIG. 6, where it may be rotated to removably lock the two elements together, or the male member 206 and slot 302' may be reversed in position as described above.

The structure of the loading device now explained, the skilled artisan will recognize the utility in effecting transition of a stent from an expanded size to a predetermined collapsed size with a predetermined diameter. Thus, the exemplary stent shown above may be slowly translated along the decreasing diameter section. As the stent is advanced, the inner walls of the decreasing diameter section 202 of loading funnel 200 exert a force that is circumferentially equal around the stent, thus enabling the stent to collapse along the points of least resistance and least stress. As discussed above, the circular and/or spiral struts will enable a predetermined, predictable and repeatable collapsing motion, leading to a predetermined, predictable and repeatable collapsed shape. When the stent has been collapsed within the constant diameter section 204 of loading funnel 200 and/or the constant diameter inner lumen of sheath 300, 300', the collapsed stent may be translated therealong to the anatomical location of interest. When the collapsed stent is released from the distal end of the inner lumen of 300, 300', it will be allowed to biasingly expand, effectively reversing the collapsing motion to reach an expanded state or configuration.

In some cases, as discussed, sheath 300, 300' may comprise a transitional sheath that provides a transition to connect with a delivery sheath or catheter comprising the same or similar inner diameter. In other cases, sheath 300, 300' may form the delivery sheath or catheter.

The loading device discussed above, e.g., loading funnel 200 and transitional sheath 300, 300', further enables a stent to be pre-loaded for use. Thus, a stent may be collapsed and loaded into the loading funnel 202 lumen, together with fluid to keep the biological and/or biologically compatible material(s) properly wetted in preparation for translation, delivery and implant.

In some embodiments, the distal end of the constant diameter section 204 (or distal end of sheath 300, 300') may be capped or plugged to hold fluid in the lumen of decreasing diameter section 202 and/or constant diameter section 204 (and/or lumen of sheath 300, 300') and in other embodiments a cap may be placed over the proximal end of decreasing diameter section 202 to further aid in holding fluid therein. This arrangement may provide a longer storage mechanism for collapsed, or partially collapsed, stents comprising moisture-sensitive, biologic material.

Alternatively, the stent may be collapsed and translated into the lumen of sheath 300, 300' as described above, filled with fluid and capped or plugged at both ends to retain fluid to assist in protecting moisture-sensitive biological material associated with the stent.

Once loaded and fluid-immersed, the stent may be held for a period of time in the collapsed configuration and/or transported to the site of need.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. A loading device for collapsing a collapsible stent in preparation for delivery and implantation into a body, the loading device comprising:
    a proximal decreasing diameter section comprising a conical outer diameter and further defining a lumen with a conical inner diameter smaller than the conical outer diameter and smoothly transitioning and ranging from a maximum diameter at a proximal end to a minimum diameter at a distal end of the proximal decreasing diameter section;
    a constant diameter section connected to, or integrated with, the proximal decreasing diameter section at the distal end of the proximal decreasing diameter section and comprising an outer diameter and further defining a lumen with an inner diameter that is substantially constant and substantially equal to the minimum diameter of the proximal decreasing diameter section, wherein the lumen of the constant diameter section extends from the distal end of the proximal decreasing diameter section to a distal end of the constant diameter section;
    a sheath comprising a lumen extending lengthwise therethrough and operatively connected to, and extending within, the lumen of the constant diameter section, the sheath comprising an outer diameter that is the same as, or smaller than, the minimum diameter of the proximal decreasing diameter section, wherein the sheath extends all the way through the lumen defined by the constant diameter section; and
    liquid disposed within the lumen of the proximal decreasing diameter section, the lumen of the constant diameter section and/or the lumen of the sheath;
    wherein the loading device is configured to collapse the collapsible stent and to deliver the collapsed stent into the lumen of the sheath;
    wherein the sheath comprises:
        a planar sheet that is adaptable to define a tubular form with an outer diameter that enables translation and/or rotation within the lumen of the constant diameter section; and
        a longitudinal slot extending along an entire length of the sheath when in the tubular form; and
    wherein the constant diameter section comprises a male member adapted to engage with, and slide within, the longitudinal slot when the sheath is translated within the lumen of the constant diameter section.

2. The loading device of claim 1, wherein relative rotation between the sheath and the constant diameter section is prevented by the engagement of the male member with the longitudinal slot.

3. The loading device of claim 1, wherein the sheath further comprises a radial slot in communication with the longitudinal slot, wherein the male member is further adapted to slide within the radial slot to prevent longitudinal translation between the constant diameter section and the sheath.

4. A method of loading and/or pre-loading a collapsible stent for the collapsing of the stent within a loading device lumen, comprising:
    providing the collapsible stent;
    providing the loading device comprising:
        a proximal decreasing diameter section defining a lumen with an inner diameter smoothly transitioning and ranging from a maximum at a proximal end to a minimum at a distal end of the proximal decreasing diameter section; and
        a constant diameter section connected to, or integrated with, the distal end of the proximal decreasing diameter section and defining a lumen with an inner diameter that is substantially equal to the minimum diameter of the proximal decreasing diameter section; and
        a sheath comprising a lumen therethrough and operatively connected to, and extending within, the lumen of the constant diameter section, the sheath comprising an outer diameter that is the same as, or smaller than, the minimum inner diameter of the proximal decreasing diameter section;
    translating the stent distally within the proximal decreasing diameter section to begin the collapsing of the stent; and
    applying pressure on the stent to translate the stent distally through the lumen of the decreasing diameter section and partially into the lumen of the constant diameter section to partially collapse the stent therein;
    wherein the sheath comprises:
        a planar sheet that is adaptable to define a tubular form with an outer diameter that enables translation and/or rotation within the lumen of the constant diameter section; and
        a longitudinal slot extending along an entire length of the sheath when in the tubular form.

5. The method of claim 4, further comprising continuing to apply pressure to distally translate the stent all the way into the lumen of the constant diameter section to completely collapse the stent therein.

6. The method of claim 5, further comprising continuing to apply pressure to distally translate the completely collapsed stent at least partially into the lumen of the sheath.

* * * * *